US011684786B2

(12) United States Patent
Sandhu et al.

(10) Patent No.: US 11,684,786 B2
(45) Date of Patent: *Jun. 27, 2023

(54) 2.4 GHZ RADIO ANTENNA FOR IMPLANTED MEDICAL DEVICES, AND ASSOCIATED SYSTEMS AND METHODS

(71) Applicant: Nevro Corp., Redwood City, CA (US)

(72) Inventors: Prabdeep Sandhu, Redwood City, CA (US); Bret Foreman, Redwood City, CA (US)

(73) Assignee: Nevro Corp., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/474,023

(22) Filed: Sep. 13, 2021

(65) Prior Publication Data

US 2022/0054846 A1    Feb. 24, 2022

Related U.S. Application Data

(63) Continuation of application No. 16/399,858, filed on Apr. 30, 2019, now Pat. No. 11,147,974.

(60) Provisional application No. 62/665,446, filed on May 1, 2018.

(51) Int. Cl.
| | | |
|---|---|---|
| *H01Q 1/27* | (2006.01) | |
| *H01Q 1/22* | (2006.01) | |
| *H01Q 1/24* | (2006.01) | |
| *H01Q 3/00* | (2006.01) | |
| *A61N 1/372* | (2006.01) | |
| *A61N 1/378* | (2006.01) | |

(52) U.S. Cl.
CPC ....... *A61N 1/37229* (2013.01); *A61N 1/3787* (2013.01); *H01Q 1/2225* (2013.01); *H01Q 1/241* (2013.01); *H01Q 1/273* (2013.01); *H01Q 3/00* (2013.01)

(58) Field of Classification Search
CPC ...... H01Q 1/241; H01Q 1/2225; H01Q 1/273; H01Q 1/40; H01Q 9/42; H01Q 3/00
See application file for complete search history.

(56) References Cited

U.S. PATENT DOCUMENTS

| | | |
|---|---|---|
| 3,871,382 A | 3/1975 | Mann |
| D250,719 S | 1/1979 | Jacobson et al. |
| 4,379,462 A | 4/1983 | Borkan et al. |
| (Continued) | | |

FOREIGN PATENT DOCUMENTS

| | | |
|---|---|---|
| WO | WO-2006131302 | 12/2006 |
| WO | WO-2011094074 A1 | 8/2011 |
| (Continued) | | |

OTHER PUBLICATIONS

International Search Report and Written Opinion for International Patent Application No. PCT/US2019/030077, dated Aug. 13, 2019, 11 pages.

(Continued)

*Primary Examiner* — Lam T Mai
(74) *Attorney, Agent, or Firm* — Perkins Coie LLP

(57) ABSTRACT

The disclosed technology provides systems and methods of communication between implanted medical devices, e.g., implanted pulse generators, and handheld consumer devices, e.g., smartphones, via standard wireless communication protocols, e.g., Bluetooth or Bluetooth Low Energy (BLE) operating in the unlicensed 2.4 GHz frequency band.

20 Claims, 10 Drawing Sheets

(56) References Cited

U.S. PATENT DOCUMENTS

| | | | |
|---|---|---|---|
| D280,930 S | 10/1985 | Speicher et al. | |
| 5,144,946 A | 9/1992 | Weinberg et al. | |
| D337,820 S | 7/1993 | Hooper et al. | |
| D343,901 S | 2/1994 | Anderson | |
| 5,300,080 A | 4/1994 | Clayman et al. | |
| 5,769,877 A | 6/1998 | Barreras, Sr. | |
| 6,104,957 A | 8/2000 | Alo et al. | |
| 6,115,634 A | 9/2000 | Donders et al. | |
| 6,522,932 B1 | 2/2003 | Kuzma et al. | |
| 6,529,774 B1 | 3/2003 | Greene | |
| 6,587,719 B1 | 7/2003 | Barrett et al. | |
| D478,990 S | 8/2003 | Kroll | |
| 6,626,181 B2 | 9/2003 | Knudson | |
| 7,047,076 B1 * | 5/2006 | Li | A61N 1/37229 343/718 |
| 7,051,419 B2 | 5/2006 | Schrom et al. | |
| D523,144 S | 6/2006 | Wenger et al. | |
| 7,133,724 B2 | 11/2006 | Greenberg et al. | |
| 7,167,743 B2 | 1/2007 | Heruth et al. | |
| 7,295,881 B2 | 11/2007 | Cohen et al. | |
| 7,308,303 B2 | 12/2007 | Whitehurst et al. | |
| D559,987 S | 1/2008 | Strother et al. | |
| 7,481,759 B2 | 1/2009 | Whitehurst et al. | |
| 7,489,968 B1 | 2/2009 | Alexander | |
| 7,502,652 B2 | 3/2009 | Gaunt et al. | |
| 7,613,524 B2 | 11/2009 | Jordan | |
| 7,616,988 B2 | 11/2009 | Stahmann et al. | |
| 7,628,750 B2 | 12/2009 | Cohen et al. | |
| 7,650,191 B1 | 1/2010 | Lim et al. | |
| D610,261 S | 2/2010 | Strother et al. | |
| 7,822,480 B2 | 10/2010 | Park et al. | |
| 7,991,483 B1 | 8/2011 | Atanasoska et al. | |
| D663,035 S | 7/2012 | Smith | |
| D665,086 S | 8/2012 | Smith | |
| D665,087 S | 8/2012 | Smith | |
| 8,929,986 B2 | 1/2015 | Park et al. | |
| D736,383 S | 8/2015 | Park et al. | |
| D736,930 S | 8/2015 | Park et al. | |
| 9,162,071 B2 | 10/2015 | Parramon et al. | |
| 9,227,076 B2 | 1/2016 | Sharma et al. | |
| 9,776,002 B2 | 10/2017 | Park et al. | |
| 10,065,044 B2 | 9/2018 | Park et al. | |
| 11,147,974 B2 * | 10/2021 | Sandhu | H01Q 1/40 |
| 2002/0107554 A1 | 8/2002 | Biggs et al. | |
| 2003/0018368 A1 | 1/2003 | Anasarinia | |
| 2003/0083697 A1 | 5/2003 | Baudino et al. | |
| 2003/0097165 A1 | 5/2003 | Krulevitch et al. | |
| 2003/0100924 A1 | 5/2003 | Foreman et al. | |
| 2003/0114752 A1 | 6/2003 | Henderson et al. | |
| 2003/0120150 A1 | 6/2003 | Govari | |
| 2003/0120322 A1 | 6/2003 | Benja-Athon | |
| 2003/0120323 A1 | 6/2003 | Meadows et al. | |
| 2003/0136418 A1 | 7/2003 | Behm | |
| 2003/0204222 A1 | 10/2003 | Leinders et al. | |
| 2004/0133184 A1 | 7/2004 | Hildebrand | |
| 2004/0186543 A1 | 9/2004 | King et al. | |
| 2005/0033393 A1 | 2/2005 | Daglow | |
| 2005/0075683 A1 | 4/2005 | Miesel et al. | |
| 2005/0113882 A1 | 5/2005 | Cameron et al. | |
| 2005/0131483 A1 | 6/2005 | Zhao et al. | |
| 2005/0134520 A1 * | 6/2005 | Rawat | A61N 1/37229 343/873 |
| 2005/0203583 A1 | 9/2005 | Twetan et al. | |
| 2005/0203584 A1 | 9/2005 | Twetan et al. | |
| 2007/0060980 A1 | 3/2007 | Strother et al. | |
| 2007/0111587 A1 | 5/2007 | Ries et al. | |
| 2007/0270916 A1 | 11/2007 | Fischell et al. | |
| 2008/0097554 A1 | 4/2008 | Payne et al. | |
| 2008/0255631 A1 | 10/2008 | Sjostedt et al. | |
| 2008/0262563 A1 | 10/2008 | Sjostedt | |
| 2009/0012576 A1 | 1/2009 | Erbstoeszer et al. | |
| 2009/0017700 A1 | 1/2009 | Zart et al. | |
| 2009/0018600 A1 | 1/2009 | Deininger et al. | |
| 2009/0228074 A1 | 9/2009 | Edgell et al. | |
| 2009/0248094 A1 | 10/2009 | McDonald | |
| 2009/0248112 A1 * | 10/2009 | Mumbru | A61N 1/37512 607/60 |
| 2009/0270948 A1 | 10/2009 | Nghiem et al. | |
| 2010/0004721 A1 | 1/2010 | Bryce et al. | |
| 2010/0038132 A1 | 2/2010 | Kinney et al. | |
| 2010/0168818 A1 | 7/2010 | Barror et al. | |
| 2010/0217340 A1 | 8/2010 | Watschke et al. | |
| 2010/0233896 A1 | 9/2010 | Dilmaghanian | |
| 2010/0305663 A1 | 12/2010 | Aghassian | |
| 2011/0087309 A1 | 4/2011 | Stypulkowski | |
| 2011/0106208 A1 | 5/2011 | Faltys et al. | |
| 2011/0112601 A1 | 5/2011 | Meadows et al. | |
| 2011/0112610 A1 | 5/2011 | Rahman et al. | |
| 2011/0270363 A1 | 11/2011 | Schramm | |
| 2012/0101551 A1 | 4/2012 | Aghassian et al. | |
| 2012/0253440 A1 | 10/2012 | Grohmann | |
| 2012/0315798 A1 | 12/2012 | Poon et al. | |
| 2013/0018440 A1 * | 1/2013 | Chow | A61N 1/37211 607/61 |
| 2013/0066399 A1 | 3/2013 | Min | |
| 2013/0085350 A1 * | 4/2013 | Schugt | A61B 5/0031 607/59 |
| 2013/0110202 A1 * | 5/2013 | Grevious | A61N 1/3605 607/60 |
| 2014/0002314 A1 * | 1/2014 | Li | H01Q 1/24 343/702 |
| 2014/0002318 A1 * | 1/2014 | Meulmester | H01Q 9/42 343/749 |
| 2018/0064945 A1 | 3/2018 | Park et al. | |
| 2018/0369595 A1 | 12/2018 | Park et al. | |
| 2019/0232064 A1 * | 8/2019 | Parker | A61N 1/36157 |
| 2019/0336776 A1 | 11/2019 | Sandhu | |
| 2019/0336778 A1 * | 11/2019 | Sandhu | H01Q 9/42 |

FOREIGN PATENT DOCUMENTS

| | | |
|---|---|---|
| WO | WO-2013067538 | 5/2013 |
| WO | WO-2016051206 | 4/2016 |

OTHER PUBLICATIONS

Extended European Search Report and Written Opinion for European Patent Application No. 19796030.5, Applicant: Nevro Corp., dated Jan. 5, 2022, 11 pages.

* cited by examiner

2.4 GHZ RADIO ANTENNA FOR IMPLANTED MEDICAL DEVICES, AND ASSOCIATED SYSTEMS AND METHODS

CROSS REFERENCE TO RELATED APPLICATION

This application is a continuation of U.S. patent application Ser. No. 16/399,858, entitled "2.4 GHZ RADIO ANTENNA FOR IMPLANTED MEDICAL DEVICES, AND ASSOCIATED SYSTEMS AND METHODS," filed on Apr. 30, 2019, now issued as U.S. Pat. No 11,147,974, which claims priority to and benefit from U.S. Provisional Patent Application No. 62/665,446, entitled "A 2.4 GHZ RADIO ANTENNA FOR IMPLANTED MEDICAL DEVICES, AND ASSOCIATED SYSTEMS AND METHODS," filed on May 1, 2018, which is hereby incorporated by reference in its entirety.

TECHNICAL FIELD

The present technology is directed generally to systems and methods for reliably communicating with implanted medical devices using handheld consumer devices and standard communication protocols such as Bluetooth and Bluetooth Low Energy (BLE) operating at the license-free 2.4 GHz frequency band.

BACKGROUND

Implantable medical devices such as spinal cord stimulators (SCS) for pain relief require radio telemetry for remote control, configuration, and monitoring. Traditionally, such radio telemetry is performed at a band specifically set aside by the Federal Communication Commission for such use, i.e., the Medical Device Radiocommunications Service (MedRadio) band at 401-406 MHz (~403 MHz). Because of the ubiquity of low cost wireless personal area networks (WPAN) such as Bluetooth and Bluetooth Low Energy (BLE) networks, and the recent proliferation of consumer devices utilizing such networks including smartphones, tablets, and laptops, it is desirable to utilize these consumer devices and networks for radio telemetry with implantable medical devices. This would eliminate the burden and cost of having a separate custom device for communicating with the implantable medical devices given that patients and medical providers would be able to do so using existing consumer devices.

However, because many of these WPANs, such as Bluetooth and BLE, operate in the license-free 2.4 to 2.4835 GHz Industrial, Scientific, and Medical (ISM) band (~2.4 GHz) as opposed to the much lower ~403 MHz MedRadio band, designing medical implants with transmitters that can effectively penetrate body tissue and receivers that can capture signals after penetrating body tissue becomes a major challenge. The challenge in designing such 2.4 GHz radiators is exacerbated by the low power and low-profile requirements of the medical implants, the penetration depth required for some implants, which can be as much as several centimeters under the surface of the patient's skin, the extra distance of the remote telemetry unit from the skin surface (which can be several meters), and the need for very reliable telemetry. Accordingly, there remains a need for improved devices and communication techniques in this technology area.

DETAILED DESCRIPTION

Figure 1A:
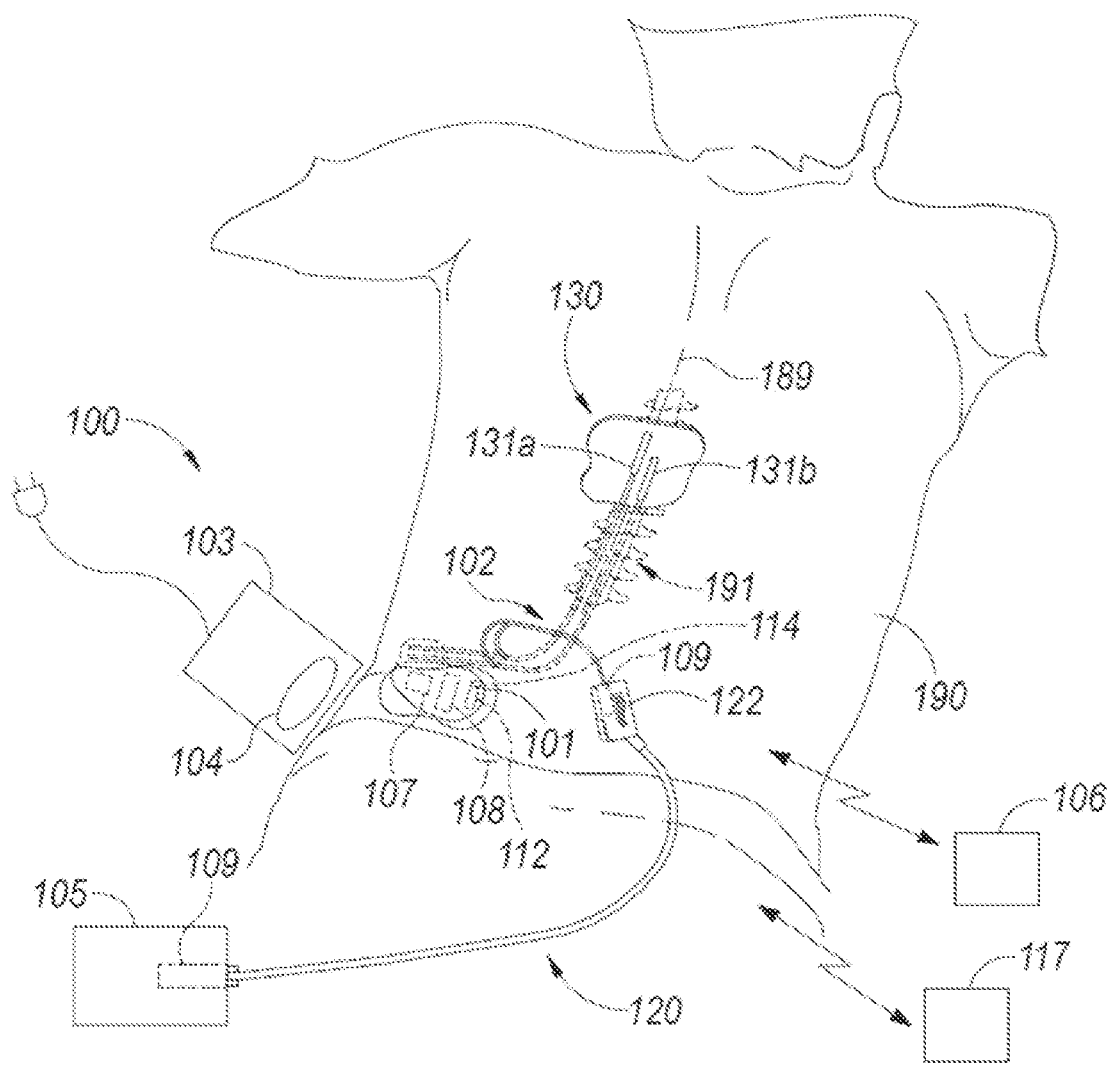
FIG. 1A is a partially schematic illustration of an implantable spinal cord modulation system positioned at the spine to deliver therapeutic signals in accordance with some embodiments of the present technology.

An overview of the disclosed technology and general aspects of the environments in which the disclosed technology operate are described below under Heading 1.0 ("Overview") with reference to FIGS. 1A, 1B, and 2. Representative embodiments of the technology are described further under Heading 2.0 ("Representative Embodiments") with reference to FIGS. 3-8. As will be discussed further below, elements of the presently disclosed technology described in the context of particular paragraphs and/or Figures may be combined with elements described in the context of other paragraphs and/or Figures. Furthermore, not all elements of the technology disclosed herein are required to practice the technology. Additionally, several details describing structures and/or processes that are well-known and often associated with integrated antennas for medical implants, but that may unnecessarily obscure some significant aspects of the present technology, are not set forth in the following description for purposes of clarity. Moreover, although the following disclosure sets forth several embodiments of the present technology, several other embodiments of the technology have different configurations or different components than those described in this section. As such, the present technology may have other embodiments, with additional elements and/or without several of the elements described below with reference to the figures. In FIGS. 1A-8, features may not necessarily be drawn to scale, and certain features may be emphasized or omitted for purposes of clarity.

1.0 OVERVIEW

FIG. 1A schematically illustrates a representative patient therapy system 100 for providing relief from chronic pain and/or other conditions, arranged relative to the general anatomy of a patient's spinal column 191. The system 100 can include a signal generator 101 (e.g., an implanted or implantable pulse generator or IPG), which may be implanted subcutaneously within a patient 190 and coupled to one or more signal delivery elements or devices 130. The signal delivery elements or devices 130 may be implanted within the patient 190, typically at or near the patient's spinal cord midline 189. The signal delivery devices 130 carry features for delivering therapy to the patient 190 after implantation. The signal generator 101 can be connected directly to the signal delivery devices 130, or it can be coupled to the signal delivery devices 130 via a signal link, e.g., a lead extension 102. In a further representative embodiment, the signal delivery devices 130 can include one or more elongated lead(s) or lead body or bodies 131 (identified individually as a first lead 131*a* and a second lead 131*b*). As used herein, the terms signal delivery device, lead, and/or lead body include any of a number of suitable substrates and/or support members that carry electrodes/devices for providing therapy signals to the patient 190. For example, the lead or leads 131 can include one or more electrodes or electrical contacts that direct electrical signals into the patient's tissue, e.g., to provide for therapeutic relief. In some embodiments, the signal delivery devices 130 can include structures other than a lead body (e.g., a paddle) that also direct electrical signals and/or other types of signals to the patient 190.

In several representative embodiments, one signal delivery device may be implanted on one side of the spinal cord midline 189, and a second signal delivery device may be implanted on the other side of the spinal cord midline 189. For example, the first and second leads 131*a*, 131*b* shown in FIG. 1A may be positioned just off the spinal cord midline 189 (e.g., about 1 mm offset) in opposing lateral directions so that the two leads 131*a*, 131*b* are spaced apart from each other by about 2 mm. The first and second leads 131*a*, 131*b* may be offset from each other axially (e.g., in a rostral-caudal direction) to provide the practitioner with a greater range of target neural populations. In particular embodiments, the leads 131 may be implanted at a vertebral level ranging from, for example, about T8 to about T12 (e.g., to treat lower back pain and/or leg pain). In other embodiments, one or more signal delivery devices can be implanted at other vertebral levels.

The signal generator 101 can transmit signals (e.g., electrical signals) to the signal delivery devices 130 that up-regulate (e.g., excite) and/or down-regulate (e.g., block or suppress) target nerves. As used herein, and unless otherwise noted, the terms "modulate," "modulation," "stimulate," and "stimulation" refer generally to signals that have either type of the foregoing effects on the target nerves. The signal generator 101 can include a machine-readable (e.g., computer-readable) or controller-readable medium containing instructions for generating and transmitting suitable therapy signals. The signal generator 101 and/or other elements of the system 100 can include one or more processor(s) 107, memory unit(s) 108, signal generation circuitry 114, and/or input/output device(s) 112. Accordingly, the process of providing modulation signals, providing guidance information for positioning the signal delivery devices 130, establishing battery charging and/or discharging parameters, and/or executing other associated functions can be performed by computer-executable instructions contained by, on, or in computer-readable media located at the pulse generator 101 and/or other system components, which may be implanted or external to the patient. Further, the pulse generator 101 and/or other system components may include dedicated hardware, firmware, and/or software for executing computer-executable instructions that, when executed, perform any one or more methods, processes, and/or sub-processes described herein; e.g., the methods, processes, and/or sub-processes described with reference to FIGS. 2-9 below. The dedicated hardware, firmware, and/or software also serve as "means for" performing the methods, processes, and/or sub-processes described herein. The signal generator 101 can also include multiple portions, elements, and/or subsystems (e.g., for directing signals in accordance with multiple signal delivery parameters), carried in a single housing, as shown in FIG. 1A, or in multiple housings.

The signal generator 101 can also receive and respond to an input signal received from one or more sources. The input signals can direct or influence the manner in which the therapy, charging, and/or process instructions are selected, executed, updated, and/or otherwise performed. The input signals can be received from one or more sensors (e.g., an input device 112 shown schematically in FIG. 1A for purposes of illustration) that are carried by the signal generator 101 and/or distributed outside the signal generator 101 (e.g., at other patient locations) while still communicating with the signal generator 101. The sensors and/or other input devices 112 can provide inputs that depend on or reflect patient state (e.g., patient position, patient posture, and/or patient activity level), and/or inputs that are patient-independent (e.g., time).

In some embodiments, the signal generator 101 and/or signal delivery devices 130 can obtain power to generate the therapy signals from an external power source 103. In one embodiment, for example, the external power source 103 can by-pass an implanted signal generator and generate a therapy signal directly at the signal delivery devices 130 (or via signal relay components). The external power source 103 can transmit power to the implanted signal generator 101 and/or directly to the signal delivery devices 130 using electromagnetic induction (e.g., RF signals). For example, the external power source 103 can include an external coil 104 that communicates with a corresponding internal coil (not shown) within the implantable signal generator 101, signal delivery devices 130, and/or a power relay component (not shown). The external power source 103 can be portable for ease of use.

In some embodiments, the signal generator 101 can obtain the power to generate therapy signals from an internal power source, in addition to or in lieu of the external power source 103. For example, the implanted signal generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

Once the implantable signal generator 101 has been positioned within the patient 190, the therapy programs provided by the signal generator 101 can be updated remotely via a wireless physician's programmer (e.g., a physician's laptop, a physician's remote or remote device, etc.) 117, and/or a wireless patient programmer 106 (e.g., a patient's laptop, patient's remote or remote device, etc.). These external devices may also be used to conduct several of the processes described later, e.g., processes for adjusting signal delivery parameters, including via responses to feedback provided by one or more sensors. Generally, the patient 190 has control over fewer parameters than does the practitioner. For example, the capability of the patient programmer 106 may be limited to starting and/or stopping the signal generator 101, and/or adjusting the signal amplitude. The patient programmer 106 may be configured to accept pain relief input as well as other variables, such as medication use.

Figure 1B:
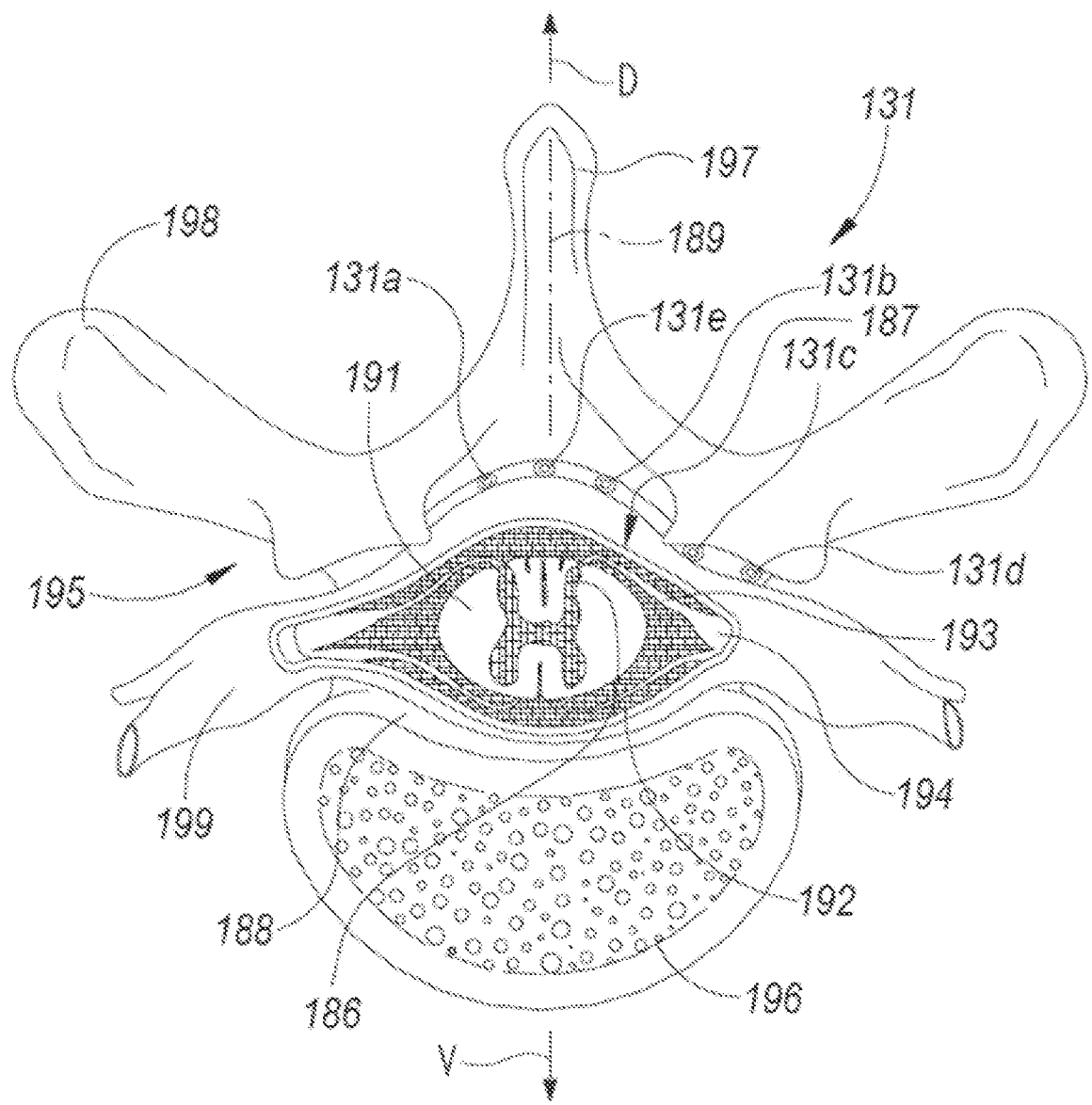
FIG. 1B is a partially schematic, cross-sectional illustration of a patient's spine, illustrating representative locations for implanted lead bodies in accordance with some embodiments of the present technology.
Figure 2:
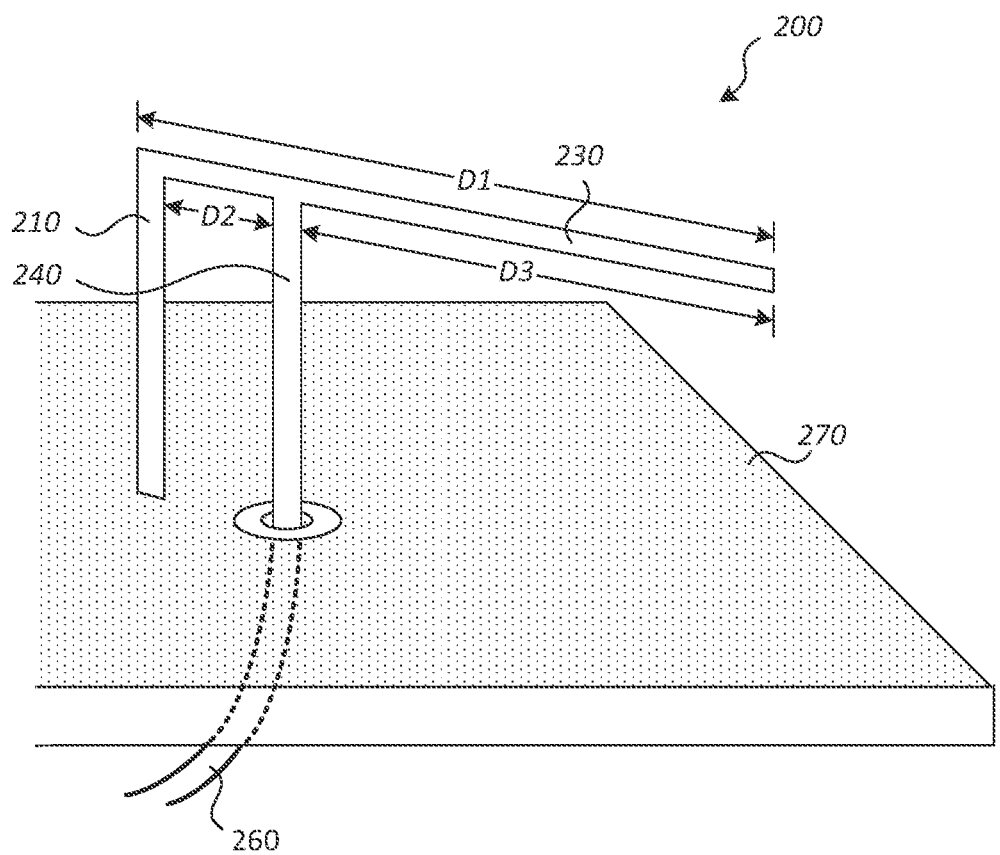
FIG. 2 is a representative illustration of a perspective view of an inverted F antenna in accordance with the prior art.

FIG. 1B is a cross-sectional illustration of the spinal cord 191 and an adjacent vertebra 195 (based generally on information from Crossman and Neary, "Neuroanatomy," 1995 (published by Churchill Livingstone)), along with multiple leads 131 (shown as leads 131a-131e) implanted at representative locations. For purposes of illustration, multiple leads 131 are shown in FIG. 1B implanted in a single patient. In actual use, any given patient will likely receive fewer than all the leads 131 shown in FIG. 1B.

The spinal cord 191 is situated within a vertebral foramen 188, between a ventrally located ventral body 196 and a dorsally located transverse process 198 and spinous process 197. Arrows V and D identify the ventral and dorsal directions, respectively. The spinal cord 191 itself is located within the dura mater 199, which also surrounds portions of the nerves exiting the spinal cord 191, including the ventral roots 192, dorsal roots 193 and dorsal root ganglia 194. The dorsal roots 193 enter the spinal cord 191 at the dorsal root entry zone 187, and communicate with dorsal horn neurons located at the dorsal horn 186. In one embodiment, the first and second leads 131a, 131b are positioned just off the spinal cord midline 189 (e.g., about 1 mm. offset) in opposing lateral directions so that the two leads 131a, 131b are spaced apart from each other by about 2 mm, as discussed above. In other embodiments, a lead or pairs of leads can be positioned at other locations, e.g., toward the outer edge of the dorsal root entry zone 187 as shown by a third lead 131c, or at the dorsal root ganglia 194, as shown by a fourth lead 131d, or approximately at the spinal cord midline 189, as shown by a fifth lead 131e.

Representative systems and methods of the present technology allow for implanted medical devices such as the implantable signal generator 101 to reliably communicate with handheld consumer devices that can operate in addition to or in lieu of the wireless physician's programmer (e.g., a physician's laptop, a physician's remote or remote device, etc.) 117, and/or a wireless patient programmer 106 (e.g., a patient's laptop, patient's remote or remote device, etc.) using the global license-free 2.4 GHz ISM, band and using common ubiquitous communication protocols such as Bluetooth (BT) and Bluetooth Low Energy (BLE). This can be in addition to or in lieu of using custom-designed receivers operating at the lower ~403 MHz MedRadio band.

FIG. 2 is a representative perspective view of a conventional inverted F antenna (IFA) 200. The conventional IFA comprises a radiating section 230, a grounding section 210 coupling the radiating section 230 to a ground 270 on a printed circuit board (PCB), and a feed section 240 coupling the radiating section 230 to an input feed 260.

The length of the radiating section 230 (first distance D1), together with the relative permittivity of the medium in which the IFA operates, determines the resonant frequency of the IFA. In order to tune the IFA to a desired resonant frequency, the length of the radiating section 230 is typically kept to about one-quarter of the wavelength of the target signal, where the wavelength depends on the relative permittivity of the medium in which the signal propagates. That is, the wavelength $\lambda = v/f$, where v is the velocity of the electromagnetic wave in the associated medium, and f is the frequency. When the electromagnetic wave propagates in free space, $v = c = 1/\sqrt{\mu_0 \varepsilon_0}$ (speed of light) where $\mu_0$ is the permeability of free space (or vacuum permeability) and $\varepsilon_0$ is the permittivity of free space (or vacuum permittivity). For example, for an IFA operating in free space and intended to transmit and receive signals at 2.4 GHz, the of the signal is about 122 mm which means that the length of radiating section 230 (first distance D1) needs to be about 30.5 cm. The grounding section 210 acts like an inductive loading of the radiating section 230, where the length of the grounding section 210 determines the amount of inductive loading and thereby adjusts the resonant frequency of the IFA from that estimated above. A second distance D2 between the feed section 240 and ground section 210 is typically kept smaller than a third distance D3 between the feed section and open end of the radiating section 230. The ratio of the second distance D2 to the third distance D3 (or how close the feed section 240 is to the grounding section 210) determines the input impedance of the IFA.

2.0 REPRESENTATIVE EMBODIMENTS

Figure 3:
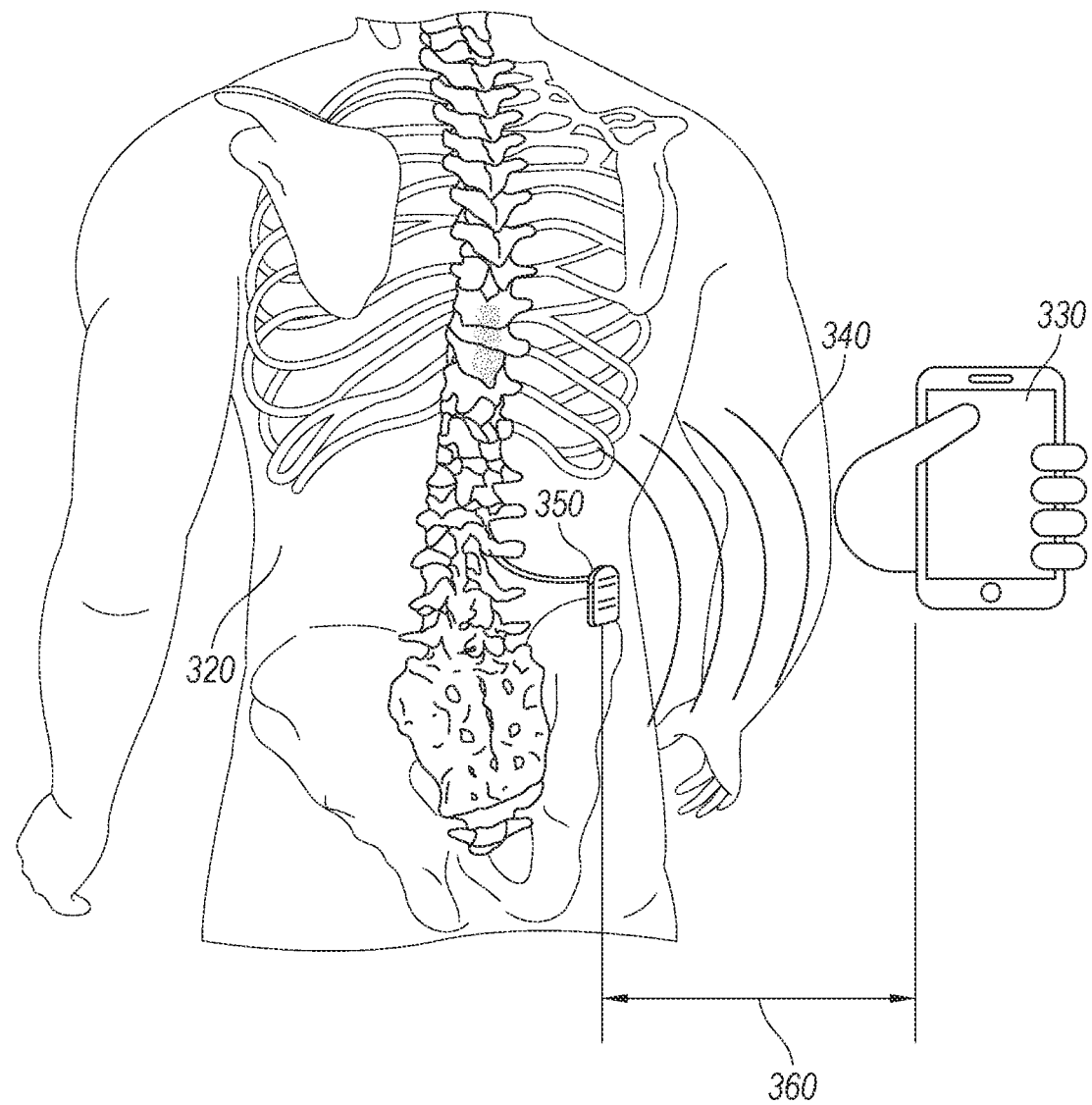
FIG. 3 is a representative illustration of a first view of an implantable medical device implanted in a human body in accordance with some embodiments of the present technology.

FIG. 3 is a representative first view of an implanted medical device 350, such as an implantable signal generator, implanted inside a human body 320. The medical device 350 communicates with a consumer wireless device 330 via radio signals 340. In a representative embodiment the radio signal 340 radiates at a frequency of between 2.4 GHz and 2.4835 GHz outside the human body 320, and is radiatively coupled to a transceiver integrated in the consumer device 330, e.g., a Bluetooth transceiver or a Bluetooth Low Energy transceiver. In one embodiment the radio signal 340 is designed to effectively be transmitted from or received by a consumer device 330 that has an offset distance 360 of as much as 2 meters away from the surface of the body 320 in which the medical device is implanted. Effective radio communication between the consumer device 330 and medical device 350 requires that the radio signal 340 have, at the consumer device 330 during reception by the consumer device or at the medical device 350 during transmission by the consumer device, sufficient signal power to overcome any noise and interference power from other users of the 2.4 GHz band. That is, the signal-to-interference-plus-noise ratio (SINR) must be sufficient for the communication protocol in use (e.g., Bluetooth) despite the radio channel conditions experienced by the radio signals as they propagate inside the human body and in free space to/from the implant.

Figure 4:
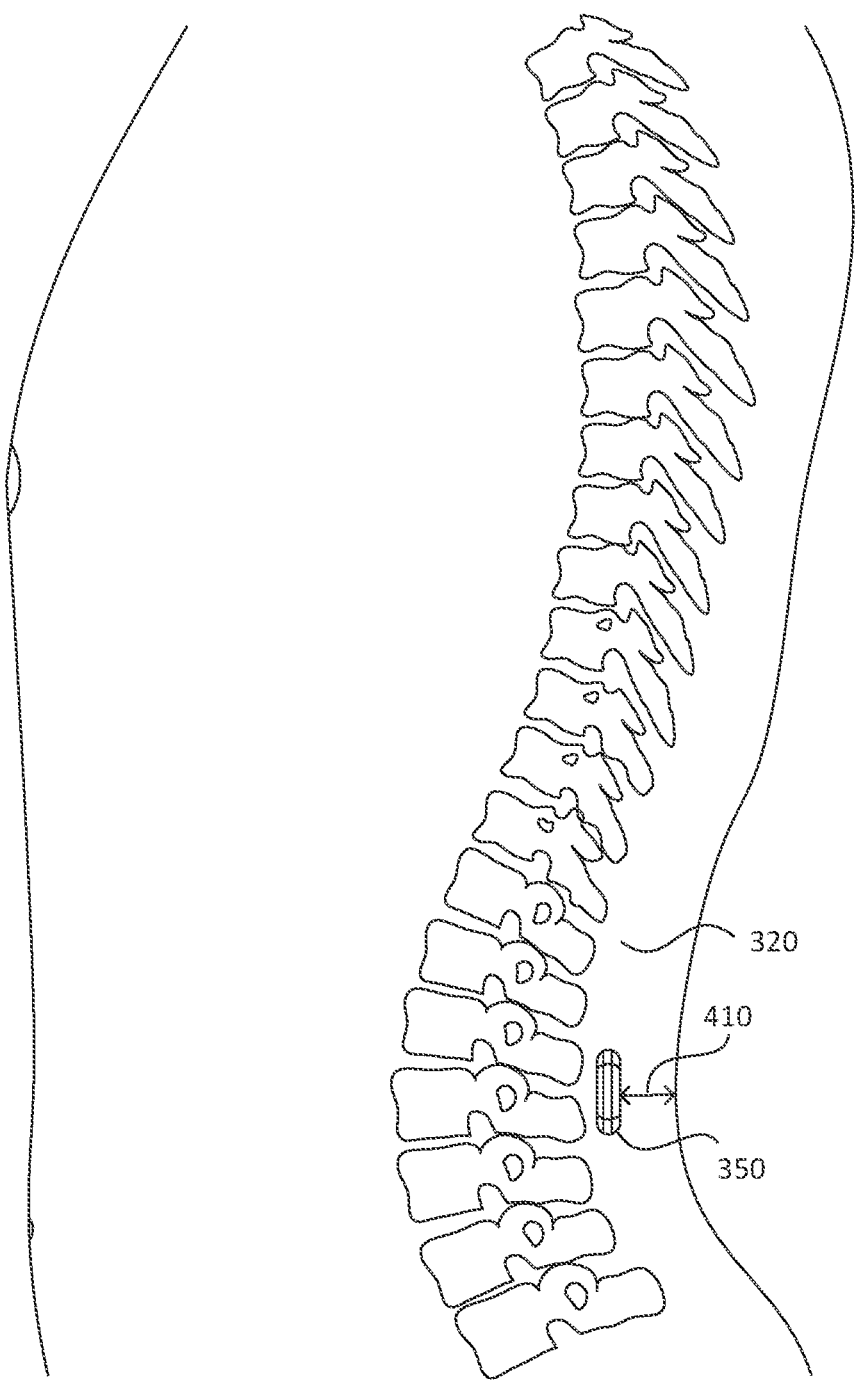
FIG. 4 is a representative illustration of a second view of an implantable medical device implanted in a human body in accordance with some embodiments of the present technology.

FIG. 4 illustrates a second view of the implanted medical device 350 implanted at a depth 410 from the surface of the skin in the body 320. In some embodiments, the depth 410 can be as much as 2.5 cm below the surface of the skin. As discussed above, the radio signal 340 is severely attenuated as it propagates from the surface of the body to the medical device 350 or from the medical device 350 to the surface of the body. In order to overcome such signal attenuation, the medical device 350 would generally need to transmit much stronger signals to effectively reach the consumer device 330, or implement receivers with much better receiver sensitivity to receive the attenuated signals from the consumer device 330. In typical radio transceivers, there is a tradeoff between transmit power or receiver sensitivity, and power dissipated by the transceiver. Additionally, the maximum amount of power radiated into the unlicensed 2.4 GHz ISM band is regulated thereby limiting the ability to arbitrarily increase the amount of power transmitted by the consumer device (e.g., by the Bluetooth radio embedded in smartphone or tablet). Furthermore, because the medical device 350 is typically a low power device, this limits the amount of power available to the communication transceiver of the implanted medical device. As a result, embodiments of the present technology include a new antenna structure to provide sufficient signal gain to overcome the losses through the body and the air interface, thereby providing for a sufficiently strong signal to be received by the implanted medical device or by the consumer device.

Figure 5A:
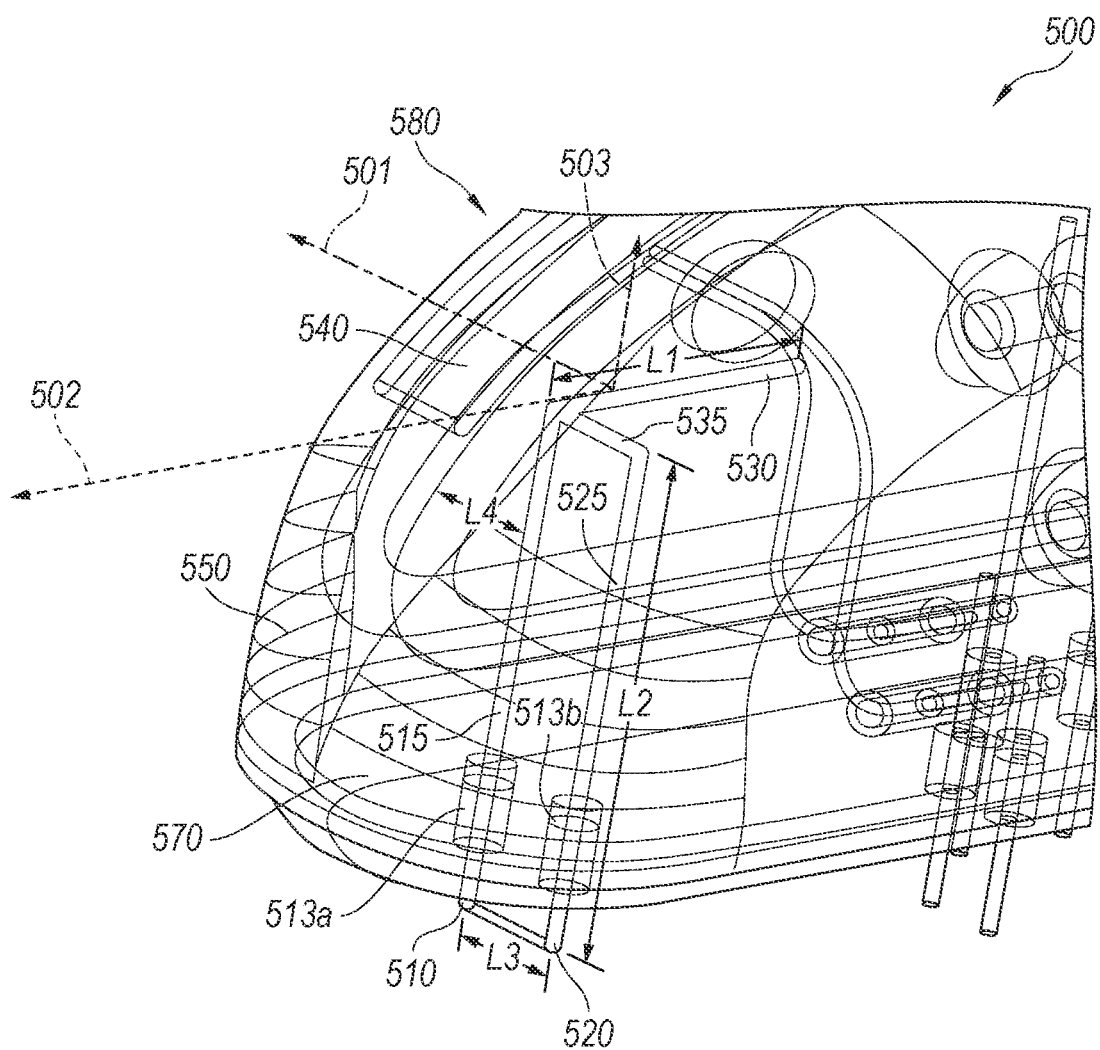
FIG. 5A is a representative illustration of a perspective view of an inverted F antenna integrated in an implantable medical device in accordance with some embodiments of the present technology.

FIG. 5A is a representative illustration of a portion of a header section 500 of an implanted medical device 350. The header section 500 includes an inverted F antenna having a grounding section 525 with a second length L2 and oriented in a z direction 503; a feed section 515, also having the second length L2, and also oriented in a z direction; a first radiating section 535 with third length L3 and oriented in the x direction 501; and a second radiating section 530 with first length L1 and oriented in the y direction 502.

The header section 500 further includes a charging coil 540 that is situated close to one side of the header section; that side will generally be the side that will be oriented towards the closest surface of the skin when the medical device is implanted. Orienting the medical device 350 with the charging coil 540 closest to the surface of the skin allows the wireless charging signals to inductively couple to the charging coil more efficiently than if the charging coil faced away from the closest surface of the skin (i.e., pointed to the main body mass). In at least some embodiments, the IFA is positioned behind and proximate to the charging coil such that it does not interfere with the inductive coupling of the charging coil to the wireless charging transmitter but also such that IFA's gain/directivity is increased (e.g., maximized) in the presence of the charging coil when compared to what the gain/directivity would be in conventional IFAs positioned proximate to a charging coil. That is, the spatial positioning, in an x, y, z direction, of the IFA inside the header 500 is selected to enhance/improve (e.g., maximize) an effective radiation property of the IFA such as the directivity of the IFA at the desired 2.4 GHz frequency band. The charging coils makes the IFA much more broadband (e.g., increases the bandwidth). For example, the IFA can be disposed at a distance to the charging coil, where the distance is selected to enhance an effective radiation property of the IFA, where "selected to enhance a radiation property" refers to positioning the IFA and the charging coil relative to each other such that the radiation property is better than it would be with the IFA alone and/or with the IFA and charging coils of conventional systems. As a result, instead of the IFA acting more like a radiator, it acts more like a coupler where the IFA is configured to couple electromagnetic radiation to the charging coil, and the charging coil is configured to radiate the coupled electromagnetic radiation toward the outer face of the header section (i.e., towards the surface of the skin to allow coupling to a handheld blue-tooth enabled mobile device).

The charging coil can additionally increase the bandwidth of the IFA, allowing the IFA to operate reliably in the entire 2.4 GHz unlicensed band (e.g., 2.4-2.4835 GHz). For example, the charging coil can enhance the standing wave ratio (SWR) or voltage SWR (VSWR) (keeping it under 2:1) or the −3 dB return loss (RL) (e.g., reduce the RL) or another property of the radiated signal to allow the radiated signal to work reliably over the desired communication band. It will be appreciated that although the charging coil is described as enhancing an effective radiation property of the IFA (e.g., directivity, gain, bandwidth, beam width such as 3 dB or half-power beam width, etc.), because the charging coil is acting as a radiator and the IFA as a coupler, the charging coil enhances a radiation property of the combined IFA and charging coil "effective antenna" radiator. That is, when the IFA converts the electrical signal at its feed to electromagnetic radiation, and the charging coil radiates the electromagnetic radiation towards the outer face of the header section, the charging coil enhances a radiation property of the electromagnetic radiation compared to the IFA acting alone with the charging coil absent. The radiator can thus be viewed as the combination of the IFA and the charging coil, unlike in conventional systems (e.g., MedRadio systems) where the radiator is primarily the antenna (e.g., loop or monopole antenna).

In a representative embodiment, the radiating section 530 is positioned a distance L4 in the x direction from the charging coil 540 where the distance L4 is about 2.2 mm. In some embodiments, the distance L4 can be constrained by other header design factors (including the space available in the header for the IFA) requiring the selection of other antenna dimensions such as L2 and L3 given a fixed L4. Additionally, if L4 is reduced to bring the feed section 515 close to the charging coil 540, the coupling coefficient between the IFA elements and the charging coil conductor can increase such that a small deviation in L4 (for example, due to manufacturing tolerances) can lead to a larger variation in the properties of the IFA.

The feed section 515 is fed (i.e., supplied with an electrical current) at feed point 510. Similarly, the grounding section 525 is grounded (i.e., electrically connected to a zero-potential node) at a ground point 520. The feed section 515 can penetrate the metallic base 570 of the header 500 through a first opening 513a. Similarly, the grounding section 525 can penetrate the metallic base 570 of the header 500 through a second opening 513b. The location of the feed section 515 relative to the grounding section 525 (i.e., the third length L3) determines the input impedance of the IFA. In representative embodiments, the third length L3 is smaller than the first length L1 of the radiating section (i.e., the feed section is closer to the grounding section than to the open end of the radiating section 530). In some embodiments, the openings 513a and 513b are insulated with a ceramic insulator. In some embodiments, the grounding and feed sections can be reversed, e.g., the IFA can be fed at the "ground point" 520, making the "grounding section" 525 the feed section, and can be grounded at the "feed point" 510, making the "feed section" 515 the grounding section.

The header section 500 can be encapsulated with medical epoxy to protect the internal components, including the IFA and charging coil. In some embodiments, the epoxy comprises a Loctite M-31 CL Hysol Medical Device Adhesive with a measured relative permittivity of about 3.12 and a measured loss tangent of about 0.04. The higher relative permittivity of the epoxy (compared to the relative permittivity of free space which is 1), together with the higher relative permittivity of muscle tissue (which could be, for example, about 52.7 with loss tangent of 0.2419 and conductivity 1.7 S/m) allow a 2.4 GHz signal to have an effectively shorter wavelength inside the body and inside the epoxy header as compared to when it is in free space. As discussed in the Overview Section 1.0 above, because of this higher relative permittivity, the velocity of the electromagnetic wave in the medium is slower, which results in a shorter wavelength signal. For example, whereas the wavelength of a 2.45 GHz signal is about 122 mm in free space, the same signal would have a wavelength of about 85 mm in a header enclosed by the epoxy fill as disclosed above and surrounded by muscle tissue. As a result, the characteristic dimensions of the IFA structure need not be as large as would be required for an equivalent IFA operating at the same frequency outside the body and not surrounded by medical epoxy. In some embodiments, to communicate using the 2.4-2.4835 GHz ISM band, the radiating section 530 has a first length L1 of about 7 mm, the radiating section 535 has a third length L3 of about 3 mm, the feed section 515 has a second length L2 of about 13 mm, and the grounding section 525 also has a second length L2 of about 13 mm. As described above, because the charging coil enhances the effective directivity and bandwidth of the IFA, the IFA can have dimensions small enough to fit in the header section 500. A small IFA additionally reduces the need to make the IFA conformal to the header section, e.g., to conform to the shape/curvature of the header (or of the housing or outer surface if the IFA is not contained in the header).

In some embodiments, during operation (e.g., when transferring data via a Bluetooth or BLE communication standard or protocol to a mobile handheld device such as a smartphone from the IPG), the IFA receives an electrical signal at the feed point 520. The electrical signal originates from a control circuit (e.g., a microcontroller) contained in the body section (described later with reference to FIG. 6). The IFA converts the electrical signal into an electromagnetic radiation signal and couples the electromagnetic radiation to the charging coil 540. As described above, the charging coil 540 is disposed in the header section proximate to an outer face of the header section (IPG oriented so that charging coil closest to surface of skin). The charging coil 540 radiates the coupled electromagnetic radiation towards the outer face of the header section (towards the outside of the body to be received by the mobile device).

The communication between the IPG and the mobile device is bi-directional so the mobile device can also transmit Bluetooth or BLE signals to the IPG. When the IPG is in reception mode, the IPG's charging coil 540 receives electromagnetic radiation from an antenna in the mobile device and couples the received electromagnetic radiation to the radiating section of the IFA. As described above, the charging coil and the IFA are configured to work together to enhance properties of the transmitted/received electromagnetic signal. For example, the effective directivity, gain, bandwidth and/or the beam width of the signal radiated by the charging coil can be enhanced/improved based on properties of the coupling between IFA and the charging coil (e.g., directivity/gain increased, bandwidth increased, and beam width decreased). For example, the distance between the charging coil and the IFA, and/or the number of turns, and/or the turns direction of the charging coil, and/or the size (e.g., radius, loop size) of the charging coil, and/or the geometry of the IFA (e.g., length of radiation sections, location of feed point, length of feed and/or grounding section, orientation of the main radiating section relative to the rest of the IFA, etc.) can be varied to vary the properties of the electromagnetic radiation radiated by the charging coil. This can result in effective antenna properties (i.e., properties of the IFA and charging coil taken together) that allow for reliable communication between the IPG and smartphone over the bandwidth in use. For example, for Bluetooth or BLE communication over the 2.4 GHz ISM band, the effective antenna properties can be antenna return loss (or VSWR or reflection coefficient) above a desired threshold over the available communication channels (e.g., for BLE over the 40 2-MHz channels, which includes three advertising channels and 37 data channels).

Figure 5B:
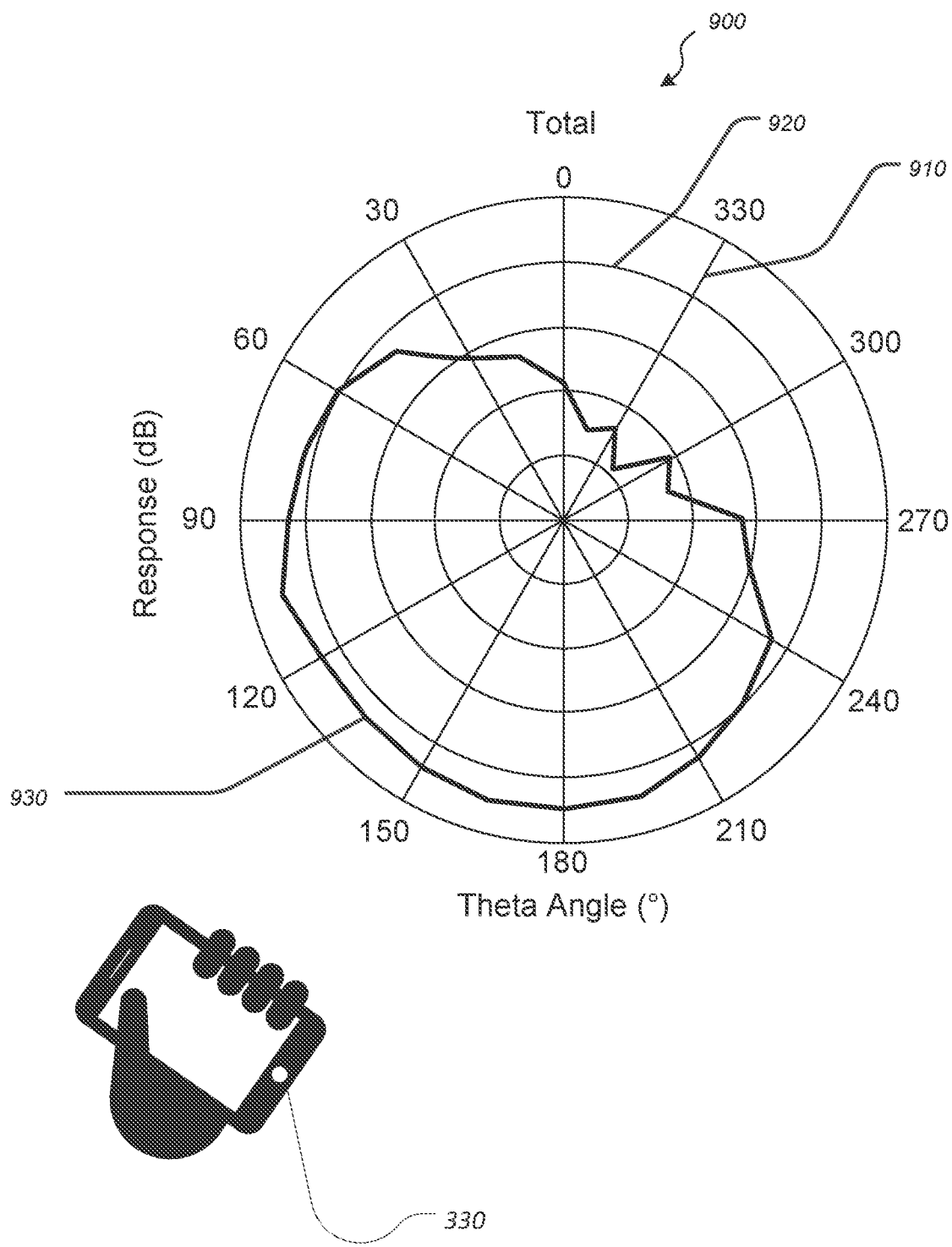
FIG. 5B is a representative plot of an antenna radiation pattern in accordance with some embodiments of the present technology.

FIG. 5B is a representative plot of an antenna radiation pattern 900 of an IFA in accordance with some embodiments of the present technology. Referring to FIGS. 5A and 5B together, the radiation pattern 900 is obtained with the IFA embedded inside the header 500 (FIG. 5A) and the header 500 implanted inside a human body, as shown in FIGS. 2 and 3. In the radiation pattern 900, the radial lines, for example, radial line 910, represents the azimuthal angle (theta angle in the horizontal plane); and the annular lines, for example, annular line 920, represents the antenna gain. In some embodiments, by positioning the radiating section 530 (FIG. 5A) inside the header 500 (FIG. 5A) at a distance L4 from the charging coil 540 (FIG. 5A) (as discussed above), implanting the medical device 350 (FIG. 3) at a depth of about 2 cm inside the body 320 (FIG. 3), the charging coil 540 (FIG. 5A) can enhance the gain of the IFA to about −35 dB as measured in the main lobe 930, where the radiation pattern 900 comprises a main beam with a 3 dB (half-power) beam width of about 90 degrees pointed toward the surface of the skin. This contrasts with the effect the charging coil would have in free space (where it acts like an interferer) resulting in a null in that direction in the resulting radiation pattern. A total integrated power gain of about −38 dB can be obtained after integrating the vertical and horizontal polarized signals of the IFA. The gain/directivity enhancement of the charging coil (e.g., "lensing effect") enables the medical device 350 (FIG. 3) to transmit a signal that can be received at consumer device 330 with sufficient signal power, without the need to increase the medical devices actual transmitter output. Additionally, it can allow the medical device 350 (FIG. 3) to receive a strong enough signal from the consumer device 330 without increasing the medical devices receiver sensitivity (which would typically require higher receiver power such as by use of lower noise and/or higher gain low noise amplifiers).

Referring now to FIG. 5A, in some embodiments, the radiating section 530 can be oriented in the z direction 503 to maintain the third distance L4 between it and the charging coil 540. Additionally, in some embodiments, the header section 500 can include metal structures made up of titanium, stainless steel, copper, and/or platinum-iridium alloy. In free space, these metallic structures in the charging coil, connector pins, and/or other components, strongly influence the antenna performance, leading to a low bandwidth and highly reactive impedance. However, when the medical device 350 is implanted such that the IFA is in the lossy tissue of the human body 320, the near field terms of the electromagnetic field dissipate, resulting in both the real and the imaginary parts of the complex antenna impedance being reduced. A reduction in the imaginary part of the antenna impedance indicates that the stored energy surrounding the antenna is reduced and most of the input energy is radiated. This means that the antenna radiation efficiency is improved. As a result, although implanting the medical device 350 into a body 320 leads to severe attenuation of the electromagnetic signal (by as much as 30 dB for a 3-cm implant depth), the lossy medium inside the human body 320 can guide or concentrate the electromagnetic wave towards the surface, due to the shape of the body 320 (which resembles a cylinder) and/or due to the relatively low electrical conductivity of the skin (about 1.7 S/m). In some embodiments, rather than implanting the medical device in the upper buttock area, which has a convex outline at the surface of the skin resembling a cylinder, the device may be implanted on other areas of the body with concave or irregular outlines. In some embodiments, the gain of the antenna in the medical device 350 improves when implanted in smaller body parts such as arms and legs away from bone structures. Various parameters of the IFA shown in FIG. 5A may be varied to adjust the antenna properties for different implant locations within the body, including, for example, varying L2 to vary the impedance, or varying L1 to adjust the gain and bandwidth to compensate for presence of bone or for different dielectric geometries.

An external lumped matching network is typically used to match the IFA to 50 ohms. Without matching, the return loss (S11) of the IFA operating at about 2.45 GHz can be about 3 dB, but after matching, the return loss can be better than 20 dB, and the impedance bandwidth can be wider than the bandwidth of the Bluetooth band with a return loss of better than 10 dB at each end of the Bluetooth band. As discussed above, different properties of the charging coil and the IFA (e.g., proximity of charging coil to the IFA) can enhance the properties of the effective antenna such as the return loss, directivity, total radiated power (TRP), or gain over the desired frequency band. In some embodiments, the gain (TRP+directivity) can be better than −20 dBi with the IPG implanted at 20 mm and transmitting a 0 dBm power. Additionally or alternatively, the return loss can be less than 10 dB (or greater than −10 dB if using a negative convention corresponding to the reflection coefficient or S11 scattering parameter) over the desired 2.4 GHz band; the TRP can be larger than −20 dBm with the IPG implanted at a depth of 3 cm and transmitting at 4 dBm over a BLE advertising channel (e.g., channel 39 centered at 2.48 GHz); and, a directivity can be greater than 5 dBi with the IPG implanted at a depth of 3 cm and transmitting at 4 dBm over a BLE advertising channel. In some embodiments, the gain of the effective antenna can be further enhanced (e.g., improved by more than 2 dB) based on the number and orientation of the therapy leads. For example, current can be coupled onto the charging coil and back to the printed circuit board through therapy leads feed pins.

It will be appreciated that although the sections 515, 525, 530, and 535 of the representative IFA are depicted as cylindrical wires in FIG. 5A, other geometries are also suitable, including planar structures which may in fact be simpler and cheaper to fabricate.

Figure 6:
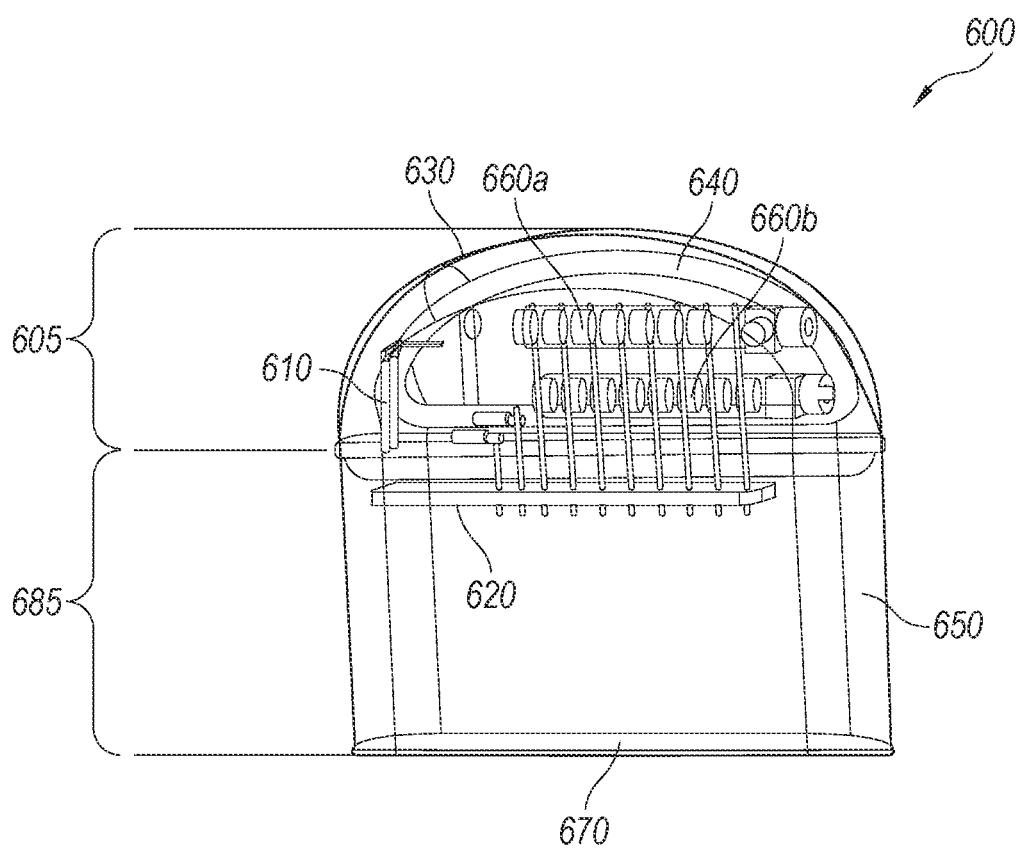
FIG. 6 is a representative illustration of an implantable medical device configured in accordance with some embodiments of the present technology.

FIG. 6 is a representative illustration of an implantable medical device 600. As discussed above, the header section 605 of the medical device 600 can be encapsulated with epoxy 630 and can include a charging coil 640 and an integrated IFA 610. The header section 605 can also include electrical contacts 660a and 660b to hold and make electrical contact with corresponding therapy leads. The IFA 610 can be coupled to a radio frequency (RF) interface printed circuit board (PCB) 620 which is contained in a titanium can 650. The feed section 515 and the grounding section 525 in FIG. 5A couple through the insulated openings 513a and 513b to the interface board 620.

The interface board 620 can provide a ground node to ground the grounding section 525 (FIG. 5A) at the ground point 520 (FIG. 5A) and a ground plane (not shown) to couple to the radiating sections of the IFA 610 which provides current return paths to support electromagnetic radiation. The ground plane is generally situated on the interface board 620 along a plane parallel to radiating sections of the IFA 610. That is, the ground plane is generally parallel to an interface between the header section and the body section. The antenna gain of the IFA 610 can be enhanced by making the ground plane as large as possible on the interface board 620.

The interface board 620 can also provide a feed point 510 (FIG. 5A) to feed the IFA 610 with the desired modulated signal and to receive the incident signal captured by the IFA for processing by circuitry in the body section 685. The impervious titanium can 650 seals the analog and RF circuitry from the environment. The metallic body of the device 650 and the baseplate 670 is floating with respect to ground.

Figure 7:
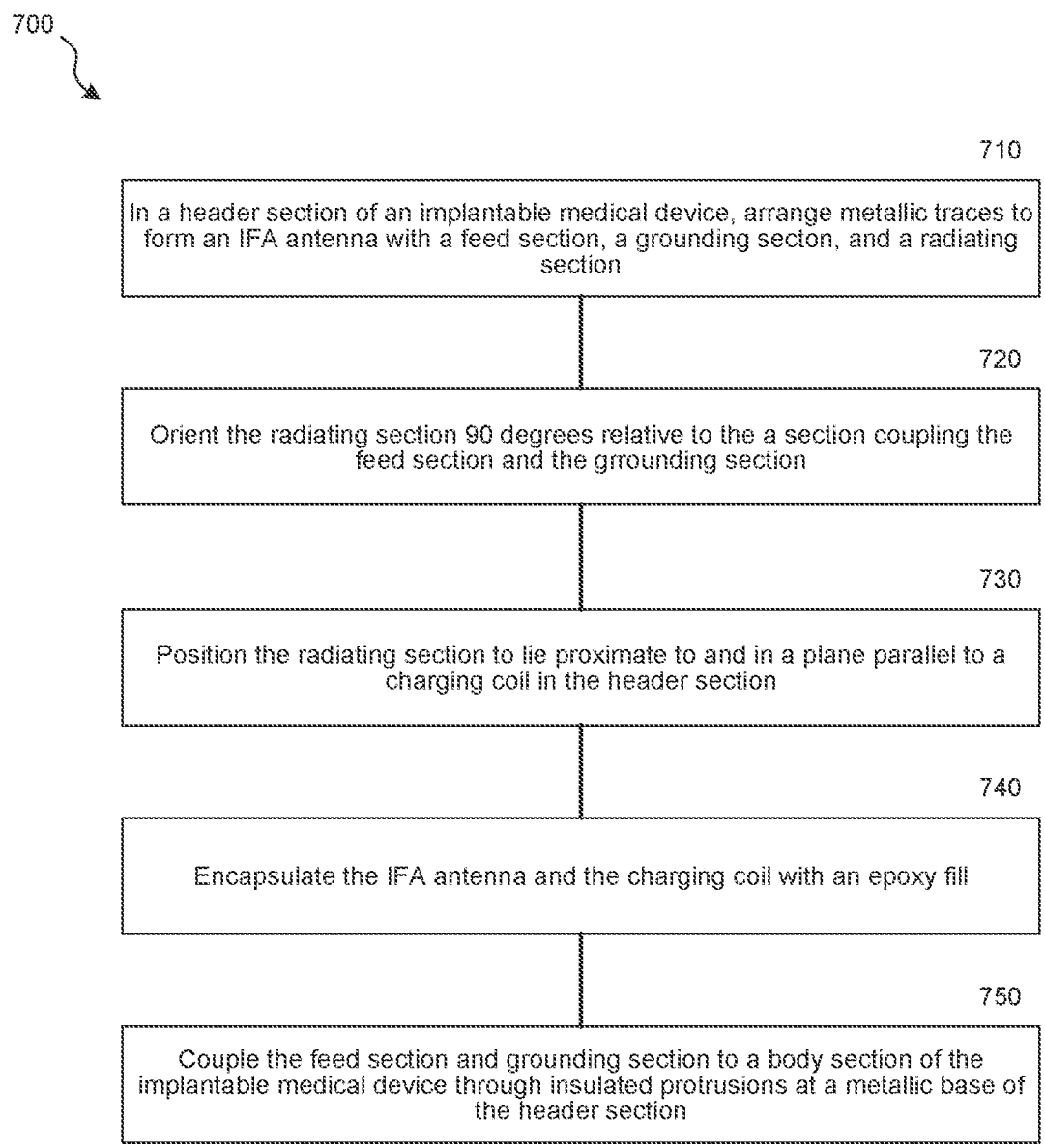
FIG. 7 is a representative flow of a process to enhance the gain of an antenna in an implantable medical device implanted in a human body, in accordance with some embodiments of the present technology.

FIG. 7 is a representative flow diagram of a process 700 for enhancing the gain of an antenna in an implantable medical device to be implanted in a human body. As discussed above, the complexity associated with designing an IFA to be integrated in an implanted medical device is exacerbated by the low power available to the medical device, the depth at which the implant is required to be implanted (and the resulting attenuation of the RF signal when propagating through the high dielectric permittivity human body to and from that depth), the distance of the handheld consumer device from the body (and the resulting attenuation of the RF signal in free space over that distance), and the small size requirements of the implanted device (which constrains the size and geometry of the IFA). To provide for a suitable IFA that is easily fabricated and assembled with high yield and reliability, a representative process at block 710 includes arranging metallic traces to form such an IFA in a header section of the medical device. The IFA comprises a radiating section, a feed section, and a grounding section. At block 720, the radiating section is oriented 90 degrees relative to the section coupling the feed section and grounding section, to allow the IFA to fit in the narrow width of the medical device. At block 730, the radiating section is positioned to lie next to, and in a plane parallel to, a charging coil in the header such that the resonance of the charging coil to the 2.4 GHz communication signal enhances the gain and/or directivity of the IFA.

At block 740, the IFA (e.g., the entire IFA), together with the charging coil, can be encapsulated with an epoxy fill. The epoxy fill can protect the IFA and charging coil from the environment inside the human body (and likewise can protect the body from the components in the header) and can also present a higher relative permittivity to the radio signal transmitted by the medical device or the consumer device communicating with the medical device. The higher permittivity of the epoxy, together with the higher permittivity of the human body (such as muscle tissue), allow for the IFA dimensions to be smaller than they would otherwise be were the medical device used outside the body or not encapsulated by epoxy.

At block 750, the feed section and grounding sections of the IFA are coupled from the header section to a body section of the medical device, e.g., through a ceramic insulating section at the metallic base of the header section. The body section includes circuitry to modulate and demodulate signals transmitted or received by the IFA and provides a grounding plane to which the grounded section is connected.

Figure 8:
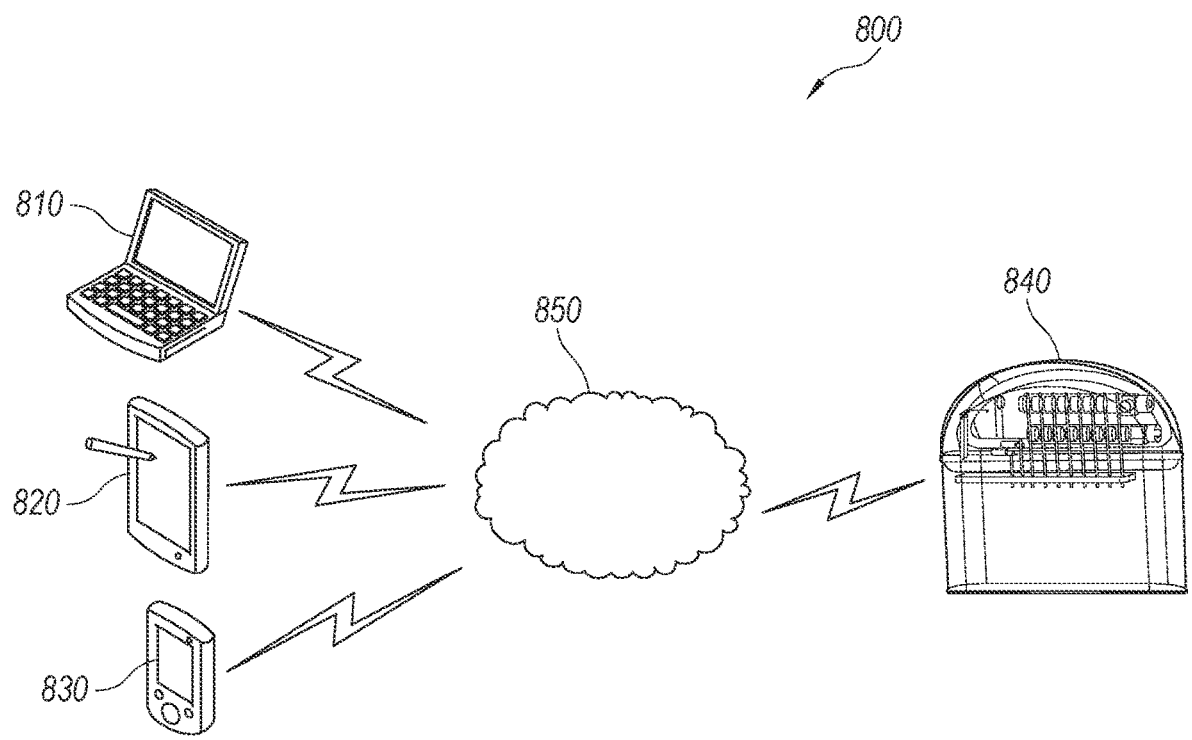
FIG. 8 illustrates a representative a representative wireless personal area network in which an implantable medical device operates in accordance with some embodiments of the present technology.

FIG. 8 and the following discussion provide a brief, general description of a suitable environment 800 in which an implanted medical device 840 may communicate with user consumer devices such as laptops 810, tablets 820, and smartphones 830 through a wireless network 850. The network 850 includes wireless personal area networks such as Bluetooth and Bluetooth Low Energy networks operating at the 2.4 GHz ISM bands. An implanted medical device 840 may communicate with server client consumer devices and each consumer device may communicate with several implanted medical devices 840.

While the present disclosure contains many representative examples, these should not be construed as limitations on the scope of any disclosed systems and/or methods or of what may be claimed, but rather as descriptions of features that may be specific to particular embodiments of particular disclosed methods. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

From the foregoing, it will be appreciated that specific embodiments of the present technology have been described herein for purposes of illustration, but that various modifications may be made without deviating from the scope of the technology. Further, while advantages associated with certain embodiments of the technology have been described in the context of those embodiments, other embodiments may also exhibit such advantages, and not all embodiments need necessarily exhibit such advantages to fall within the scope of the present technology. Accordingly, the present disclosure and associated technology can encompass other embodiments not expressly shown or described herein.

As used herein, the phrase "and/or," as in "A and/or B" refers to A alone, B alone, and A and B. As used herein, the terms "generally" and "about" when used to describe numeric values refer to values within 10% of the indicated value.

To the extent any materials incorporated herein by reference conflict with the present disclosure, the present disclosure controls.

The following clauses describe representative implementations of the present technology.

Clause 1. An implantable medical device (IMD), comprising: a header section, comprising: a charging coil disposed proximate to one outer face of the header section; an inverted F antenna (IFA) disposed proximate to the charging coil and further from the outer face of the header section than the charging coil, wherein the IFA comprises a grounding section, a feed section, a first radiating section, and a second radiating section, the first radiating section coupling the grounding section to the feed section, the second radiating section being disposed in a plane parallel to the charging coil and perpendicular to the first radiating section, and the second radiating section being longer than the first radiating section; an epoxy fill encapsulating the charging coil and IFA; and a base section disposed in a plane perpendicular to and below the charging coil; a body section coupled to the header section and housing circuitry; and an insulation section disposed between the base section of the header section and the body section, comprising insulated openings allowing the feed section and the grounding section of the IFA to penetrate the base section of the header section and to electrically couple to the circuitry in the body section.

Clause 2. The implantable medical device of clause 1, wherein the feed section is about 13 mm in length, the grounding section is about 13 mm in length, the first radiating section is about 3 mm in length, the second radiating section is about 7 mm in length, and the second radiating section is disposed between 2 and 3 mm from the charging coil.

Clause 3. The implantable medical device of any of the foregoing clauses, wherein the body section comprises a ground plane disposed along a plane parallel to the base section, and wherein the second radiating section is in a plane parallel to the ground plane.

Clause 4. The implantable medical device of any of the foregoing clauses, wherein the IFA is not conformal to the header section.

Clause 5. The implantable medical device of any of the foregoing clauses, wherein the IFA is configured to couple electromagnetic radiation to the charging coil and the charging coil is configured to radiate the coupled electromagnetic radiation toward the one outer face of the header section.

Clause 6. The implantable medical device of any of the foregoing clauses, wherein the epoxy fill has a relative permittivity that is generally 3.12, and a loss tangent that is generally 0.04 and is composed of LOCTITE M-31CL Hysol Medical Device Adhesive.

Clause 7. The implantable medical device of any of the foregoing clauses, wherein the IFA is disposed at a distance to the charging coil selected to enhance an effective radiation property of the IFA.

Clause 8. The implantable medical device of clause 7, wherein the effective radiation property is an antenna directivity.

Clause 9. The implantable medical device of any of clauses 7 or 8, wherein the antenna directivity is greater than 5 dBi when the implantable medical device is implanted at a depth of 3 cm, the implantable medical device transmits a signal at a power of 4 dBm and a frequency channel corresponding to a Bluetooth Low Energy advertising channel.

Clause 10. The implantable medical device of clause 7, wherein the effective radiation property is an antenna gain.

Clause 11. The implantable medical device of clause 7, wherein the effective radiation property is an antenna half power beam width.

Clause 12. The implantable medical device of clause 7, wherein the effective radiation property is an antenna bandwidth.

Clause 13. The implantable medical device of any of the clauses 7 or 12, wherein the antenna bandwidth corresponds to a bandwidth in which the return loss is less than 10 dB.

Clause 14. The implantable medical device of any of the clauses 7, 12 or 13, wherein the bandwidth in which the return loss is less than 10 dB corresponds to a bandwidth including a frequency range between 2.4 GHz to 2.4835 GHz.

Clause 15. A method of coupling an implantable medical device to a hand-held device, the method comprising: receiving an electrical signal at a feed point of an inverted F antenna (IFA), wherein the IFA is disposed in a header section of the implantable medical device; converting, at the IFA, the electrical signal to electromagnetic radiation; coupling the electromagnetic radiation to a charging coil disposed proximate to one outer face of the header section; and, radiating, by the charging coil, the electromagnetic radiation towards the one outer face of the header section, wherein the charging coil enhances a radiation property of the electromagnetic radiation.

Clause 16. The method of clause 15, further comprising: receiving, at the charging coil, an electromagnetic signal transmitted by the hand-held device; and, coupling the electromagnetic signal to a radiating section of the IFA.

Clause 17. The method of any of the foregoing clauses, wherein the electrical signal transports data to and from a control circuit disposed in a body section of the implantable medical device, wherein the data conforms to a Bluetooth or Bluetooth Low Energy communication protocol.

Clause 18. The method of clause 16, wherein the hand-held device is a mobile phone configured to transmit and receive electromagnetic signals conforming to a Bluetooth or Bluetooth Low Energy communication standard.

Clause 19. The method of clause 15, wherein a first property of the electromagnetic radiation radiated by the charging coil towards the one outer face of the header section is based on a second property of the electromagnetic radiation coupled to the charging coil from the IFA.

Clause 20. The method of any of clauses 15 or 19, wherein the first property is at least one of a directivity, a gain, a bandwidth, or a beam width and the second property is based on at least one of a distance between the IFA and the charging coil, a size of the charging coil, a number of turns of the charging coil, and a size of the IFA.

We claim:

1. An implantable medical device, comprising:
   a header section, comprising:
      a coil disposed proximate to an outer face of the header section, wherein the coil is configured to inductively couple to a wireless power transmitter; and
      an inverted F antenna (IFA) disposed proximate to the coil and further from the outer face of the header section than the coil, wherein the IFA comprises a grounding section, a feed section, a first radiating section, and a second radiating section, the first radiating section coupling the grounding section to the feed section.

2. The implantable medical device of claim 1, wherein the second radiating section is disposed in a plane parallel to the coil and perpendicular to the first radiating section.

3. The implantable medical device of claim 1, wherein the IFA is not conformal to the header section.

4. The implantable medical device of claim 1, wherein the IFA is configured to couple electromagnetic radiation to the coil.

5. The implantable medical device of claim 1, wherein the header section further comprises an epoxy fill encapsulating the coil and the IFA.

6. The implantable medical device in claim 1, wherein the IFA is disposed at a distance to the coil selected to enhance an effective radiation property of the IFA.

7. The implantable medical device of claim 6, wherein the effective radiation property is an antenna directivity.

8. The implantable medical device of claim 7, wherein the antenna directivity is greater than 5 dBi when the implantable medical device is implanted at a depth of 3 cm, and the implantable medical device transmits a signal at a Bluetooth frequency channel.

9. The implantable medical device of claim 6, wherein the effective radiation property is an antenna gain or an antenna half power beam width.

10. The implantable medical device of claim 6, wherein the effective radiation property is an antenna bandwidth.

11. The implantable medical device of claim 10, wherein the antenna bandwidth corresponds to a bandwidth in which the return loss is less than 10 dB.

12. The implantable medical device of claim 11, wherein the bandwidth in which the return loss is less than 10 dB corresponds to a bandwidth including a frequency range between 2.4 GHz to 2.4835 GHz.

13. A method of coupling an implantable medical device to an external device, the method comprising:
   receiving an electrical signal at a feed point of an inverted F antenna (IFA), wherein the IFA is disposed in a header section of the implantable medical device;
   converting, at the IFA, the electrical signal to electromagnetic radiation;
   coupling the electromagnetic radiation to a coil disposed proximate to an outer face of the header section, wherein the coil is configured to inductively couple to a wireless power transmitter; and,
   radiating, by the coil, the electromagnetic radiation towards the outer face of the header section, wherein the coil enhances a radiation property of the electromagnetic radiation.

14. The method of claim 13, further comprising:
   receiving, at the coil, an electromagnetic signal transmitted by the external device; and,
   coupling the electromagnetic signal to a radiating section of the IFA.

15. The method of claim 13, wherein the electrical signal transports data to and from a control circuit disposed in a body section of the implantable medical device, wherein the data conforms to a Bluetooth or Bluetooth Low Energy communication protocol.

16. The method of claim 14, wherein the external device comprises a mobile phone configured to transmit and receive electromagnetic signals conforming to a Bluetooth or Bluetooth Low Energy communication standard.

17. The method of claim 13, wherein a first property of the electromagnetic radiation radiated by the coil towards the outer face of the header section is based on a second property of the electromagnetic radiation coupled to the coil from the IFA.

18. The method of claim 17, wherein the first property is at least one of a gain, or a bandwidth and the second property is based on at least one of a distance between the IFA and the coil, or a number of turns of the coil.

19. The implantable medical device of claim 1, wherein the coil is configured to radiate electromagnetic radiation toward the outer face of the header section.

20. The implantable medical device of claim 1, wherein an effective radiation property of the IFA is enhanced by a number or an orientation of a therapy lead of the implantable medical device.

* * * * *

UNITED STATES PATENT AND TRADEMARK OFFICE
CERTIFICATE OF CORRECTION

PATENT NO. : 11,684,786 B2
APPLICATION NO. : 17/474023
DATED : June 27, 2023
INVENTOR(S) : Prabdeep Sandhu et al.

Page 1 of 1

It is certified that error appears in the above-identified patent and that said Letters Patent is hereby corrected as shown below:

In the Specification

In Column 6, Line 3, after "the" insert -- $\lambda$ --.

In the Claims

In Column 15, Line 38, in Claim 6, delete "in" and insert -- of --.

Signed and Sealed this
Twenty-second Day of August, 2023

Katherine Kelly Vidal
*Director of the United States Patent and Trademark Office*